US00PP24661P3

(12) United States Plant Patent
Brazelton et al.

(10) Patent No.: US PP24,661 P3
(45) Date of Patent: Jul. 22, 2014

(54) BLUEBERRY PLANT NAMED 'CARGO'

(50) Latin Name: ***Vaccinium corymbosum* hybrid**
Varietal Denomination: Cargo

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 150 days.

(21) Appl. No.: 13/385,902

(22) Filed: Mar. 12, 2012

(65) Prior Publication Data

US 2013/0239260 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

(56) References Cited

U.S. PATENT DOCUMENTS

PP10,035 P 9/1997 Moore

OTHER PUBLICATIONS

Pluto Upov Plant Variety Database 2013/03, retrieved on Sep. 24, 2013. Retrieved from the Internet at <http://www.upov.int/pluto/en/index.jsp> Citation for *Vaccinium* 'Cargo', 3 pp.*

* cited by examiner

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'Cargo' is provided. 'Cargo' is a commercial variety intended to be machine harvested for both the fresh and processed markets. The variety has a very uniform crop of medium sized fruit with good flavor and excellent firmness, and has consistently high yields. 'Cargo' is a vigorous plant, with a narrow crown and upright growing habit, and has an estimated chilling requirement of 800 to 1,000 hours.

3 Drawing Sheets

Latin name of the family, genus, and species: Family—Ericaceae. Genus—*Vaccinium.* Species—*corymbosum* hybrid.

Variety denomination: The new blueberry plant claimed is of the variety denominated 'Cargo.'

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry known as a *Vaccinium corymbosum* hybrid referred to as 'Cargo,' as herein described and illustrated.

The new blueberry plant variety 'Cargo' was selected in Lowell, Oreg. in 2005. 'Cargo' is a commercial variety intended to be machine harvested for both the fresh and processed markets. The variety has a very uniform crop of medium sized fruit with good flavor and excellent firmness, and has consistently high yields. 'Cargo' is a vigorous plant, with a narrow crown and upright growing habit, and has an estimated chilling requirement of 800 to 1,000 hours.

Pedigree and History: The new blueberry plant originated from a cross of 'Bluegold' (female parent, unpatented) by 'Ozarkblue' (pollen parent, U.S. Plant Pat. No. 10,035). The new blueberry plant variety 'Cargo' has been planted in replicated trials since 2006.

The new variety can be compared to commercial variety 'Liberty' (U.S. Plant Pat. No. 15,146) in that 'Cargo' ripens about one week earlier, and does not have problems with cane dieback or wrinkling fruit.

The new variety can be compared to commercial variety 'Draper' (U.S. Plant Pat. No. 15,103) in that 'Cargo' has a higher yield with smaller fruit, a more upright, vigorous growing habit, and ripens 2 to 3 weeks later.

The new blueberry plant variety 'Cargo' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Cargo' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'Cargo':

1. Uniform crop of light blue, medium sized fruit.
2. Consistent, high yields.
3. Vigorous plant with narrow crown and upright growth habit.

BRIEF DESCRIPTION OF THE DRAWINGS

The accompanying photographic illustration shows typical specimens in full color of the foliage and fruit of the new variety 'Cargo.' The colors are a nearly true as is reasonably possible in a color representation of this type.

BOTANICAL DESCRIPTION

Figure 1:
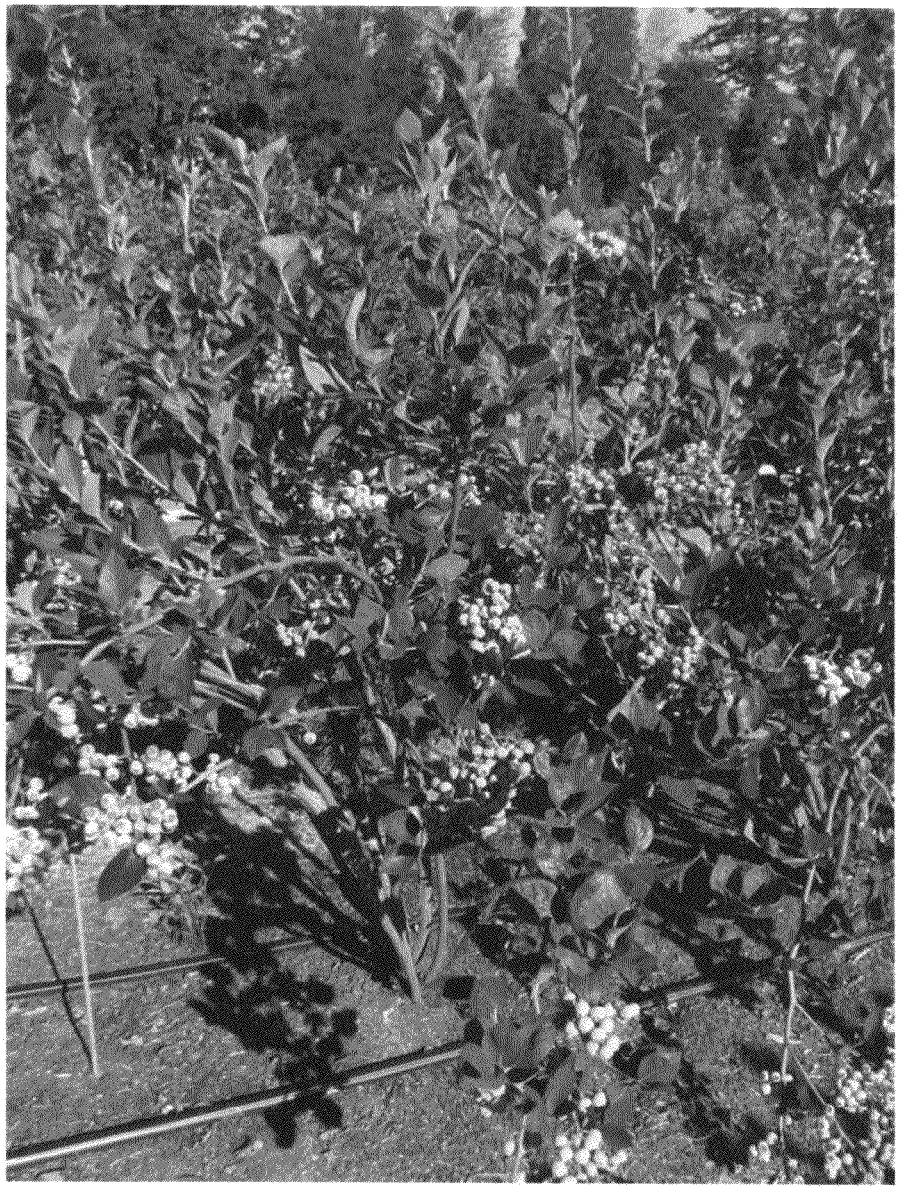
FIG. 1 is a photograph of the new variety 'Cargo.'
Figure 2:
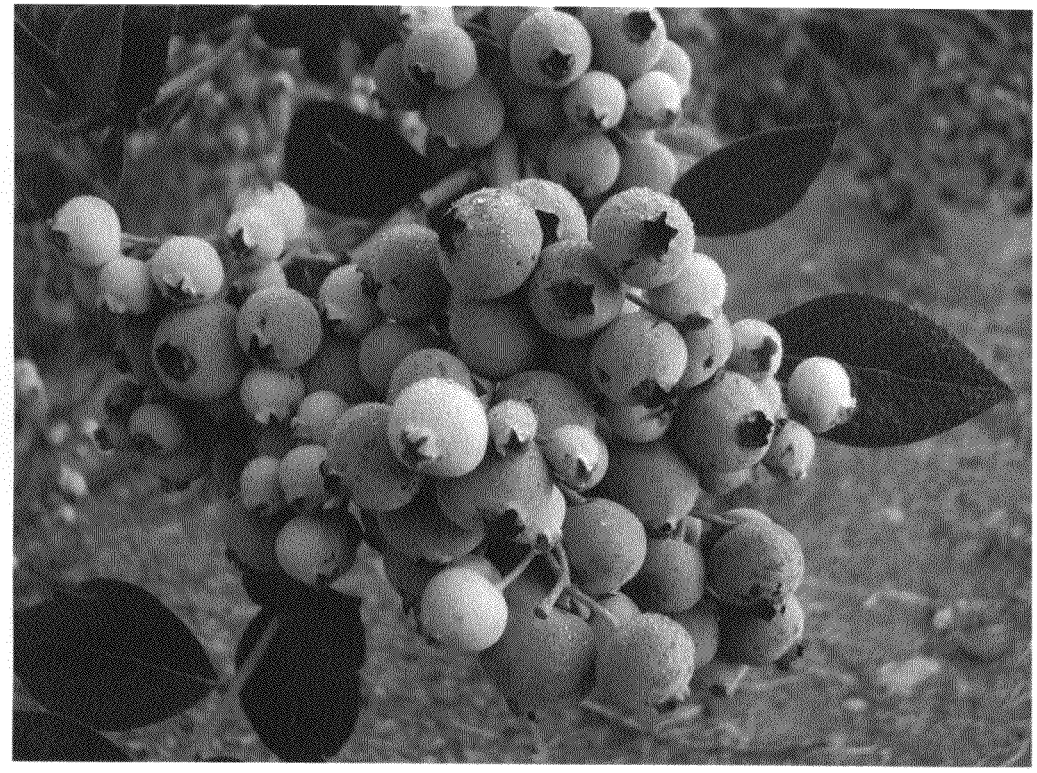
FIG. 2 is a photograph of the fruit of the new variety 'Cargo.'
Figure 3:
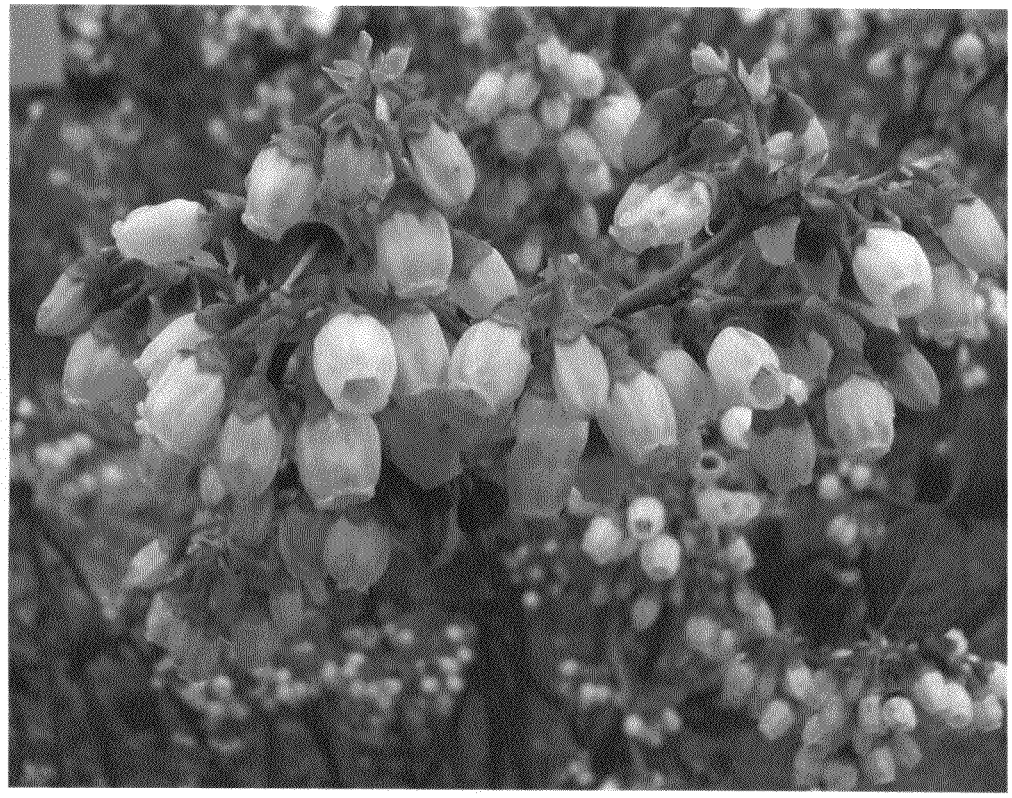
FIG. 3 is a photograph of the flowers of the new variety 'Cargo.'

The following detailed description sets forth the distinctive characteristics of 'Cargo.' The data which defines these characteristics was collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:

*a. Family.*—Ericaceae.
*b. Genus.*—*Vaccinium.*
*c. Species.*—*corymbosum* hybrid.
*d. Common name.*—Northern Highbush Blueberry.

Parentage:

*Female parent.*—Bluegold (unpatented).
*Male parent.*—Ozarkblue (U.S. Plant Pat. No. 10,035).

Market class: 'Cargo' is a commercial variety intended to be machine harvested for both the fresh and processed markets.

PLANT

Plant size:

*a. Height of plant.*—Average of 54 inches.
*b. Canopy diameter.*—Average of 36 inches.

Growth habit: Upright.
Plant vigor: Vigorous.
Twigginess: Low.
Suckering: Low.
Evergreenness: Deciduous.
Chilling requirement: Approximately 800-1000 hours.
Cold hardiness: Approximately USDA zones 4-7.
Productivity in Lowell:

*a.* 3 *year old.*—Heavily pruned plants produced an average of 6.38 lbs per plant, compared to Liberty plants (pruned normally) of the same age, which produced and average of 7.46 lbs per plant.
*b.* 4 *year old.*—Heavily pruned plants produced an average of 7.97 lbs per plant, compared to Liberty plants (pruned normally) of the same age, which produced an average of 8.9 lbs per plant.
*c.* 5 *year old.*—Normally pruned plants produced an average of 16.09 lbs per plant.

Propagation: Easy to propagate from softwood cuttings.
Disease and pest resistance/susceptibility:

*a. Root rot* (*Phytophthora cinnamomi*).—Does not appear to be overly susceptible.
*b. Stem blight* (*Botryosphaeria spp*).—Undetermined.
*c. Phomopsis twig blight* (*Phomopsis vaccinii*).—Does not appear to be overly susceptible.
*d. Botryosphaeria stem canker* (*Botryosphaeria corticis*).—Undetermined.
*e. Bacterial cane canker* (*Pseudomonas syringae*).—Does not appear to be overly susceptible.
*f. Botrytis blight* (*Botrytis cinerea*).—Does not appear to be overly susceptible.
*g. Leaf spot* (*Septoria spp.*).—Does not appear to be overly susceptible.
*h. Leaf rust* (*Naohidemyces vaccinii*).—Does not appear to be overly susceptible.
*i. Bud mites* (*Acalatus vaccinii*).—Undetermined.

Disease survival: Good.

TRUNK AND BRANCHES

Texture:

*a. Surface texture new wood.*—Smooth.
*b. Surface texture* 1 *yr wood.*—Smooth.
*c. Surface texture* 3 *yr wood.*—Rough.

Color:

*a. Color of new wood.*—Pantone color Apple Green 15-1543.
*b. Color of rough bark* 1 *year.*—Pantone color Green Banana 14-0434 and Willow 16-0632.
*c. Color of rough bark* 3 *year.*—Pantone colors Cocoa Brown 18-1222, Smoke Gray 14-1209, and Moonlight 15-1309.

FOLIAGE

Internode length: Average of 22.87 mm.
Leaf dimensions:

*a. Leaf length.*—Average of 62.34 mm.
*b. Leaf width.*—Average of 38.96 mm.

Leaf shape: Elliptical with acute apex and base.
Leaf margin: Entire.
Leaf color:

*a. Upper leaf surface mature leaves.*—Pantone Chive 19-0323.
*b. Upper leaf surface new leaves.*—Pantone Peridot 17-0336, Baked Apple 18-1648 and Crushed Berry 18-1418.
*c. Lower leaf surface.*—Pantone color Water Cress 17-0220.

Fall foliage color: Pantone Eggplant 19-231.
Pubescence:

*a. Pubescence upper leaf surface.*—Absent.
*b. Pubescence lower leaf surface.*—Absent.
*c. Pubescence leaf margins.*—Absent.

Petiole:

*a. Average petiole length.*—Average of 3.12 mm.
*b. Petiole color.*—Pantone color Lettuce Green 13-0324.
*c. Petiole surface texture.*—Smooth.

Leafing vs flowering: Flower bud break occurs prior to vegetative bud break in Lowell, Oreg. Flowers persist during initial vegetative growth period.

FLOWERS

Flower arrangement: Alternate arrangement.
Immature flower color: Pantone color Claret Red 17-1740 and Snow White 11-0602.
Fragrance: Sweet, faint.
Flower shape: Urceolate to cylindrical.
Pollen:
- *a. Pollen staining*.—Approximately 95% viable, Staining with 2% acetocarmine dye.
- *b. Pollen abundance*.—High.
- *c. Pollen color*.—Pantone color Pale Banana 12-0824.

Flower length: Average 10.31 mm.
Corolla:
- *a. Corolla length*.—Average of 7.26 mm.
- *b. Corolla diameter*.—Average of 7.24 mm.
- *c. Corolla aperture*.—Average of 3.87 mm.
- *d. Corolla color*.—Pantone color Antique White 11-0105.
- *e. Corolla texture*.—Smooth.

Style length: Average of 6.94 mm.
Calyx:
- *a. Calyx diameter*.—Average of 4.35 mm.
- *b. Calyx surface*.—Smooth.
- *c. Calyx color*.—Pantone color Spinach Green 16-0439.

Pistil color: Pantone color Apple Green 15-0543.
Pedicel:
- *a. Pedicel color*.—Pantone color Green Olive 17-0535 and Rose Wine 17-1623.
- *b. Pedicel length flower*.—Average of 8.32 mm.

Peduncle:
- *a. Peduncle color*.—Pantone color Green Olive 17-0535.
- *b. Peduncle length flower*.—Average of 15.26 mm.

Anther:
- *a. Anther length*.—Average of 6.08 mm.
- *b. Anther color*.—Pantone color Burnt Orange 16-1448.

Stigma location: Stigma even with lip of corolla, and up to 0.15 mm above lip of corolla, on average.
Flowering cluster: Loose flowering cluster, high density.
Flowering period: Begins flowering in mid-April, reaching 50% bloom during the last week of April or the first week of May and continues flowering through mid-May.
Number flowers: Average of 10-12 flowers per cluster.
Self-compatibility: Very good—on average 90% of self-pollinated flowers reach maturity.
Average inflorescence size: 33.89 mm.

BERRIES

Mean harvest date: August 7.
Mean date last pick: September 5.
Calyx:
- *a. Calyx aperture*.—Average of 4.46 mm.
- *b. Calyx lobes*.—5 lobes, slightly pronounced.
- *c. Calyx depth*.—Average of 2.24 mm.

Berry cluster: Loose.
Berries per cluster: Average of 8-10.
Berry pedicel:
- *a. Length*.—Average of 10.26 mm.
- *b. Surface texture*.—Smooth.

Berry peduncle:
- *a. Length*.—Average of 26.13 mm.
- *b. Peduncle surface texture*.—Smooth.

Berry detachment: Easy.
Berry weight: Average berry weight over 2 years was 2 g, compared to Liberty, which had an average berry weight over 2 years of 1.79 g.
Berry height: Average of 13.69 mm.
Berry width: Average of 17.56 mm.
Berry shape: Round.
Berry color:
- *a. Immature berry color*.—Pantone color Leaf Green 15-0332.
- *b. Berry skin color on plant*.—Pantone color Dapple Gray16-3907.
- *c. Berry skin color after harvest*.—Pantone color Velvet Morning 18-3927.
- *d. Berry skin color after polishing*.—Pantone color Dark Navy 19-4013.

Berry wax: Moderately heavy and persistent.
Berry flesh color: Pantone color Asparagus Green 12-0311.
Pedicel scar: Small and dry, average of 2.9 mm in diameter.
Berry firmness: Firm. Average berry firmness as measured on a Firmtech fruit firmness testing machine was 185.65 g/mm of deflection, compared to Liberty plants harvested on the same day which had an average of 160.93 g/mm of deflection.
Berry flavor: Sweet and tart, good balance.
Berry texture: Firm.

SEEDS

Seed color: Pantone color Madder Brown 19-1331.
Seed length: Average of 1.89 mm.
Seed width: Average of 1.27 mm.
Seed weight: Average of 0.5 mg.
Quantity seeds per berry: Average of 48 seeds per berry.

DISTINGUISHING FEATURES FROM MALE PARENT 'OZARKBLUE'

TABLE 1

| Name of paternal parent | Characteristic(s) in which the candidate variety differs from the paternal parent | Describe the expression of the characteristic for the paternal parent | Describe the expression of the characteristic for 'Cargo' |
|---|---|---|---|
| Ozarkblue | Average time of 50% open flowers in Lowell, Oregon | April 28 | May 6 |
| Ozarkblue | Leaf length | 53 mm | 74 mm |

The invention claimed is:

1. A new and distinct variety of blueberry plant named 'Cargo,' substantially as illustrated and described herein.

* * * * *